United States Patent [19]
Nakano, deceased et al.

[11] Patent Number: 5,349,860
[45] Date of Patent: Sep. 27, 1994

[54] APPARATUS FOR MEASURING THE THICKNESS OF CLAD MATERIAL

[75] Inventors: Tetsuo Nakano, deceased, late of Kawasaki, by Kazuko Nakano, legal representative; Takeshige Katsumata, Kawasaki; Megumu Tanaka, Kawasaki; Isao Narushima, Kawasaki; Yoshiharu Hirano, Kawasaki; Kazuko Nakano, Takaoka, all of Japan

[73] Assignee: NKK Corporation, Tokyo, Japan

[21] Appl. No.: 882,455

[22] Filed: May 12, 1992

Related U.S. Application Data

[63] Continuation-in-part of Ser. No. 771,513, Oct. 1, 1991, which is a continuation of Ser. No. 591,752, Oct. 2, 1990, abandoned.

[30] Foreign Application Priority Data

Nov. 28, 1989 [JP] Japan .................. 1-306468

[51] Int. Cl.$^5$ ........................................ G01N 29/10
[52] U.S. Cl. ...................................... 73/597; 73/612; 73/622; 73/624; 364/563
[58] Field of Search ................ 73/597, 598, 609, 610, 73/612, 614, 615, 620, 621, 622, 624, 627, 629; 364/563

[56] References Cited

U.S. PATENT DOCUMENTS 4,003,244  1/1977  O'Brien et al. ................ 73/597
4,098,131  7/1978  Renzel ........................... 73/627
4,334,433  6/1982  Takahashi ...................... 73/629
4,513,621  4/1985  Renzel et al. .................. 73/627
4,538,469  9/1985  Lynnworth et al. ............. 73/597
4,624,127  11/1986  Narushima et al. ............. 73/610
4,669,310  6/1987  Lester ........................... 73/597
4,918,989  4/1990  Desruelles et al. ............. 73/627

FOREIGN PATENT DOCUMENTS 62-116256  5/1987  Japan .

Primary Examiner—Tom Noland
Assistant Examiner—Rose M. Finley
Attorney, Agent, or Firm—Frishauf, Holtz, Goodman & Woodward

[57] ABSTRACT

An apparatus for measuring the thickness of a clad material having an outer mother metal and an inner clad metal. The apparatus includes a transmitter crystal and a receiver crystal of a double crystal angle-type probe which contact the outer surface of the mother metal, for receiving a first echo from the boundary surface of the mother metal and clad metal, and for receiving a second echo from the inner, bottom surface of the clad metal. The apparatus further includes an amplifier for amplifying the echo signals, a detector for detecting the zero-crossing points of the echoes, a zero point determining circuit, a calculator for calculating the periods from a zero point in time to the zero-crossing points, and a calculator for calculating the thickness of the clad material and clad metal based on the calculated periods.

17 Claims, 6 Drawing Sheets

APPARATUS FOR MEASURING THE THICKNESS OF CLAD MATERIAL

CROSS REFERENCE TO RELATED APPLICATION

This is a continuation-in-part application of Ser. No. 07/771,513 filed Oct. 1, 1991, which is a Continuation of Ser. No. 07/591,752 filed Oct. 2, 1990, now abandoned.

BACKGROUND OF THE INVENTION

1. Field of the Invention

This invention relates to the field of measuring technology, and more particularly to the field of measuring the thickness of clad material such as clad metal.

2. Description of the Related Arts

Generally speaking, so called "clad materials" in steel technology means clad metals wherein a base metal made of low carbon steel or low alloyed steel, hereafter mother metal, is clad on one or both sides by an anti-corrosive metal such as a stainless steel or a nickel base alloy, hereafter clad metal.

Generally the clad surface is metallurgically connected. The thickness of the clad metal, hereafter clad thickness, the thickness of the mother metal, and the total thickness or the thickness of the mother metal plus the clad thickness, hereafter the total thickness, should be accurately measured.

As for the method of measuring these thicknesses, a measuring technique using an optical method is proposed wherein the end sections of a clad product are cut, polished and observed by a microscope.

Japanese Utility Model laid open Nos. 73205/1987 and 143205/1982 propose methods of measuring the thickness wherein the total thickness is measured by an ultrasonic thickness meter and the clad thickness is measured by an eddy current thickness meter, or a film thickness meter. As for the former method, for instance, when the ends of a clad material are cut, polished, and observed by a microscope, a yield loss is generated due to the cutting, and a considerable amount of time is required for the measuring.

Moreover, it is impossible to measure the thicknesses of the clad material with respect to its whole length. As for the latter method, when this measuring method is applied to a clad tube wherein a clad part is inserted into the inside of a mother tube, the total thickness is measured by the ultrasonic thickness meter from the outside of the clad tube, and the clad thickness is measured by the eddy current thickness meter utilizing the principle of a film thickness meter from the inside of the clad tube. Due to the principle of measurement, the clad metal is restricted to a nonmagnetic one. To carry out the measurement, a sensor of the eddy current thickness meter should be inserted into the clad tube which requires a considerable facility with a considerable mechanism. In the measuring operation, the insertion and taking out of the sensor requires a considerable amount of time.

Especially when a long clad tube is measured by this device, the mechanism for the inserting and the positioning of the sensor requires a considerable facility and the positioning is so difficult that the discrepancy of the measured points between the sensor of the eddy current thickness meter and that of the total thickness meter needs to be corrected.

SUMMARY OF THE INVENTION

It is an object of the present invention to provide an apparatus for measuring the thickness of clad material. It is a further object of the present invention to provide an apparatus for measuring the thickness of clad metal. It is another object of the present invention to provide a non-destructive measuring apparatus whereby the thicknesses can be measured with high accuracy and responsiveness, especially of a clad tube.

The apparatus of the present invention is provided for measuring the thickness of clad material which comprises a clad metal and a mother metal, said clad metal having an outer surface and an inner surface, said mother metal having an outer and an inner surface, and said clad metal being clad to said mother metal such that the outer surface of said clad metal and the inner surface of said mother metal form a boundary surface.

The apparatus of the present invention comprises a double crystal angle probe which contacts the outer surface of said mother metal. The double crystal angle probe includes a transmitter crystal means for radiating a plurality of ultrasonic beams into said clad material, and a receiver crystal means. The receiver crystal means is provided for receiving a first echo of an ultrasonic beam from the boundary surface of said mother metal and clad metal, for receiving a second echo of the ultrasonic beam from the inner surface of said clad metal, and for producing first and second echo signals, respectively.

The apparatus of the present invention further comprises amplifying means for amplifying said first echo signal with a first amplitude value, and for amplifying said second echo signal with a second amplitude value, said amplifying means being responsive to first and second time sharing signals for alternately amplifying said first and second echo signals with said first amplitude value and said second amplitude value.

The apparatus of the present invention still further comprises zero point determining means for determining a zero point of time when the transmitter crystal means radiates an ultrasonic beam into said clad material, time sharing means for generating said first time sharing signal and said second time sharing signal at predetermined timings, and gating means for gating said amplified first echo signal and said amplified second echo signal.

The apparatus of the present invention still further comprises detecting means for detecting a time when said amplified first echo signal reaches a first zero-crossing point after a peak of said amplified first echo signal, and for detecting a time when said amplified second echo signal reaches a first zero-crossing point after a peak of said amplified second echo signal.

The apparatus of the present invention still further comprises period calculating means for calculating a first time period from the zero point of time determined by said zero point determining means to the first zero-crossing point of said amplified first echo signal, and for calculating a second time period from the zero point of time to the first zero-crossing point of said amplified second echo signal.

The apparatus of the present invention still further comprises thickness calculating means for calculating the thickness of said clad metal and the total thickness of said clad material as a function of said calculated first time period and said calculated second time period.

DETAILED DESCRIPTION

Figure 1:
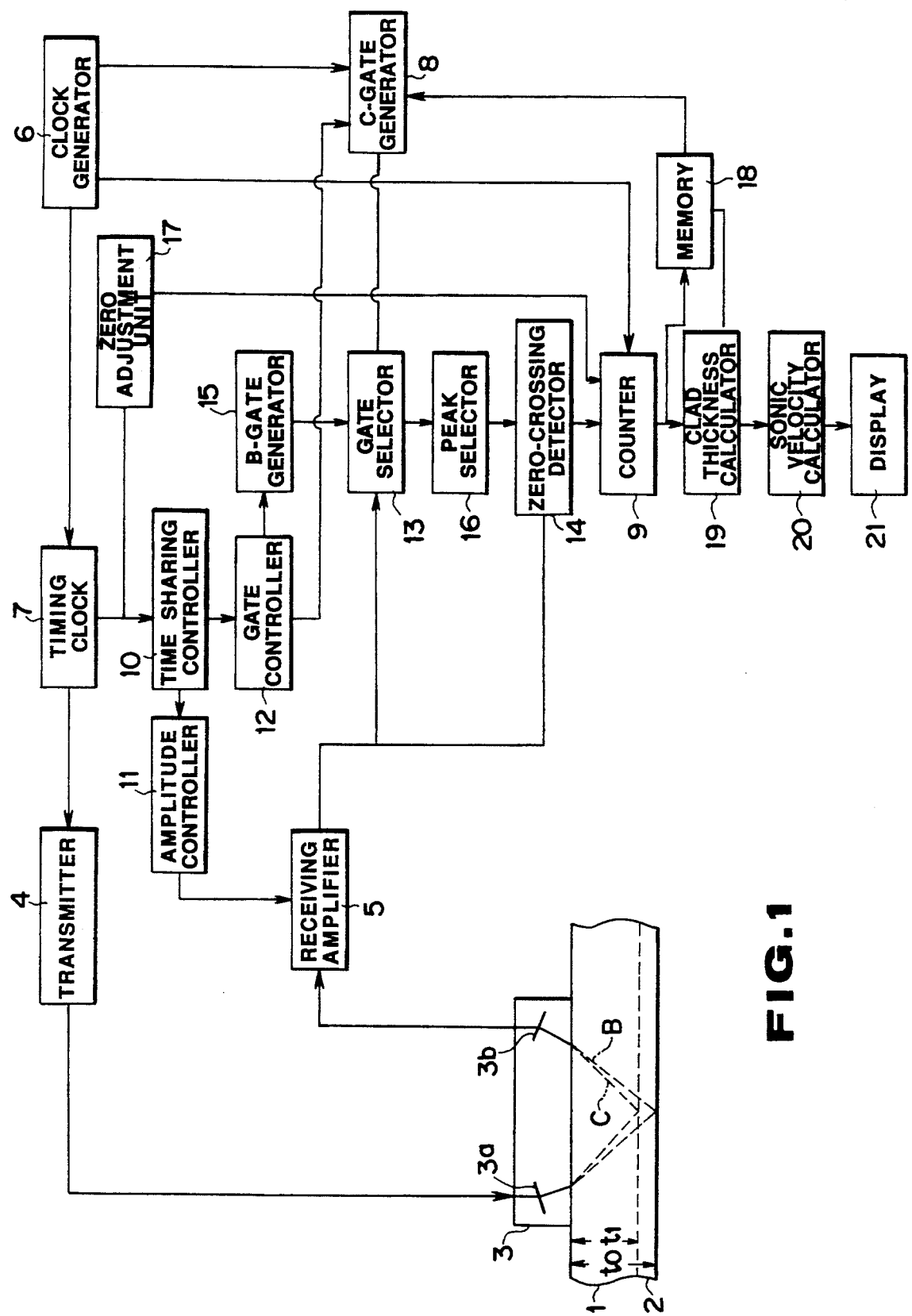
FIG. 1 is a flow chart of an embodiment of the invention.
Figure 7:
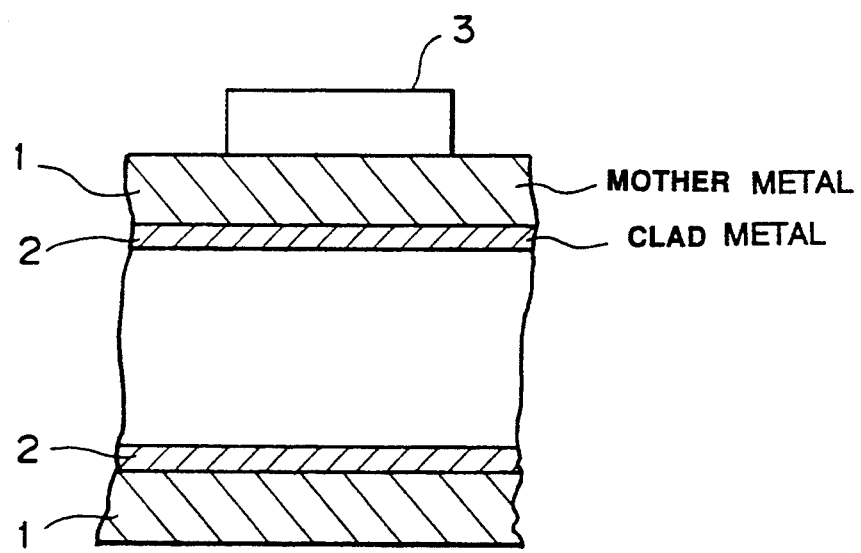
FIG. 7 shows a longitudinal sectional view of a clad tubular material whose thickness can be measured by the apparatus of the present invention.
Figure 8:
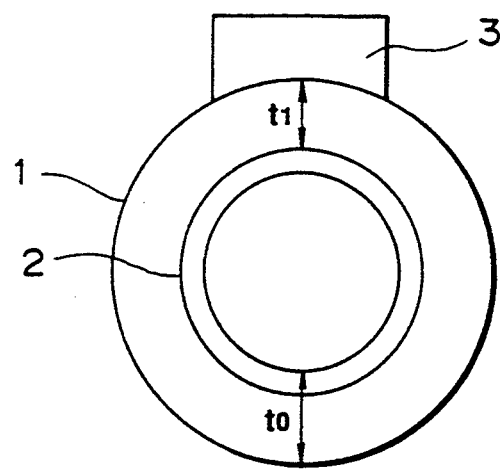
FIG. 8 shows a side view of the clad tubular material shown in FIG. 7.

FIG. 1 illustrates a block diagram of an embodiment of the invention. The clad material whose thickness is to be measured, as shown in FIG. 7, comprises a mother metal 1 and a clad metal 2. The outer surface of the clad metal 2 is clad to an inner surface of the mother metal 1, and as shown in FIG. 8, the material is, for example, in the shape of a tube. A double crystal angle probe 3 is contacted to an outer surface of the clad metal 2.

Figure 2A:
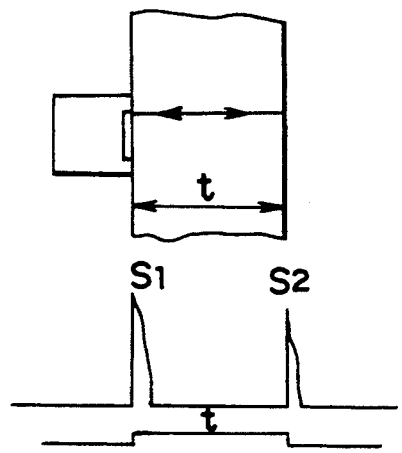
FIGS. 2A and 2B are explanatory views of conventional ultrasonic thickness meters utilizing compression wave.
Figure 2B:
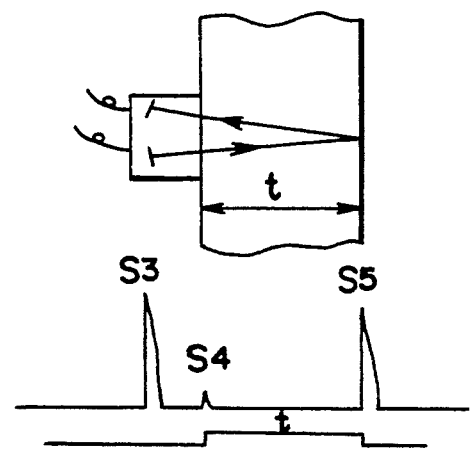

FIGS. 2A and 2B are explanatory views of conventional ultrasonic thickness meter utilizing a compression wave. FIG. 2A shows a single probe technique and FIG. 2B shows a double probe technique. Both Figures show schematic views of the path of the sonic beam, at the top, the signal pattern of the echo signal, at the middle, and the signal pattern of the detection gate which is set to detect the echo from the boundary of the mother metal and the clad metal, hereafter the clad surface, at the bottom.

In the case of the single probe technique of FIG. 2A the clad thickness is obtained by measuring the time interval between the transmitting of the transmitting pulse $S_1$ and the receiving of the echo $S_2$. In the case of the double probe technique of FIG. 2B the clad thickness is obtained by measuring the time interval between the receiving of the surface echo $S_4$ and bottom echo $S_5$ after the transmitting pulse $S_3$ is transmitted. Both methods utilize compression waves.

As a method of utilizing a shear wave, a normal probe of a Y cut crystal transducer utilizing the shear wave is well known. However, due to the restriction of a contacting media consisting of a liquid wherein the shear wave cannot be transmitted, automatic measurement in use of the liquid media is not possible.

The sonic pressure reflective coefficient from the clad surface is given by the following equations.

$$r_{12}(\%) = P_2/P_1$$
$$= (Z_1 + Z_2)$$
$$Z_1 = P_1 \cdot C_1$$
$$Z_2 = P_x \cdot C_2,$$

wherein $P_1$ and $P_2$ are the density of the metal, $C_1$ and $C_2$ represent the sonic velocity, and $Z_1$ and $Z_2$ represent the acoustic impedance.

Table 1 shows the sonic pressure reflective coefficient of the material calculated from the acoustic impedance thereof. As shown in Table 1, the sonic pressure reflective coefficient of the clad surface is high in the case of the shear wave compared with the compression wave. Actually, the level of the echo is recognizable in the case of the shear wave, but the level is too low to be differentiated with noise in the case of the compressional wave.

TABLE 1

| Kinds of Clad Metals | Shear Wave | Compression Wave |
|---|---|---|
| Nickel Alloy Clad I | 1.8 | 0.5% |
| Nickel Alloy Clad II | 1.6% | 0.4% |
| Stainless Steel Clad I | 1.5% | 1.0% |
| Stainless Steel Clad II | 1.2% | 0.6% |

Based on the aforementioned information, in the present invention, a shear wave is utilized, being generated by a double crystal angle probe, wherein the echo at the clad surface is comparatively large and the echo at the clad surface can be recognizable by a calculating means, whereby the thickness of the mother metal and the total thickness can be measured. The difference between the above two thickness is the clad thickness. This is the measurement technique of the present invention.

The double crystal angle probe 3 in FIG. 1 is equipped with a transmitter crystal 3a and a receiver crystal 3b, and the distance between the points of incidence thereof is determined by the thickness of the metal to be measured in case of the angle of refraction being in the range of 35°–70°.

In the embodiment of FIG. 1, the angle of refraction is set at 38°. The depth of the focus of the ultrasonic beam is determined by this distance, and the level of the echo varies with the depth. The transmitter crystal 3a is connected to a transmitter 4, and the receiver crystal 3b is connected to a receiver amplifier 5.

A clock generator 6 generates a clock signal for measuring the ultrasonic path length. The clock signal is transmitted to the timing clock 7, gate generator 8, and counter 9.

The timing clock 7 receives the clock signal and transmits the timing signal of transmission to the transmitter 4 and to the time sharing controller 10.

The transmitter 4 receives the timing signal of transmission and generates an ultrasonic pulse so that the transmitter crystal 3a generates an ultrasonic beam. The time sharing controller 10 receives the timing signal of transmission from the timing clock 7, generates the time sharing signal at the timing at which the receiver crystal 3b receives the echo from the boundary surface C between the inner surface of the mother metal and the outer surface of the clad metal, hereafter called the clad echo, and the echo from the inner (i.e., bottom) surface of the clad metal B, hereafter called the total echo, and transmits the timing signal to the amplitude controller 11 and the gate controller 12.

The amplitude controller 11 receives the timing signals, alternately the amplitude responsive to the total echo B and the clad echo C. The receiving amplifier 5 amplifies the signals of the total echo B and the clad echo C in accordance with the alternation so that the level of the two signals agree.

Figure 3:
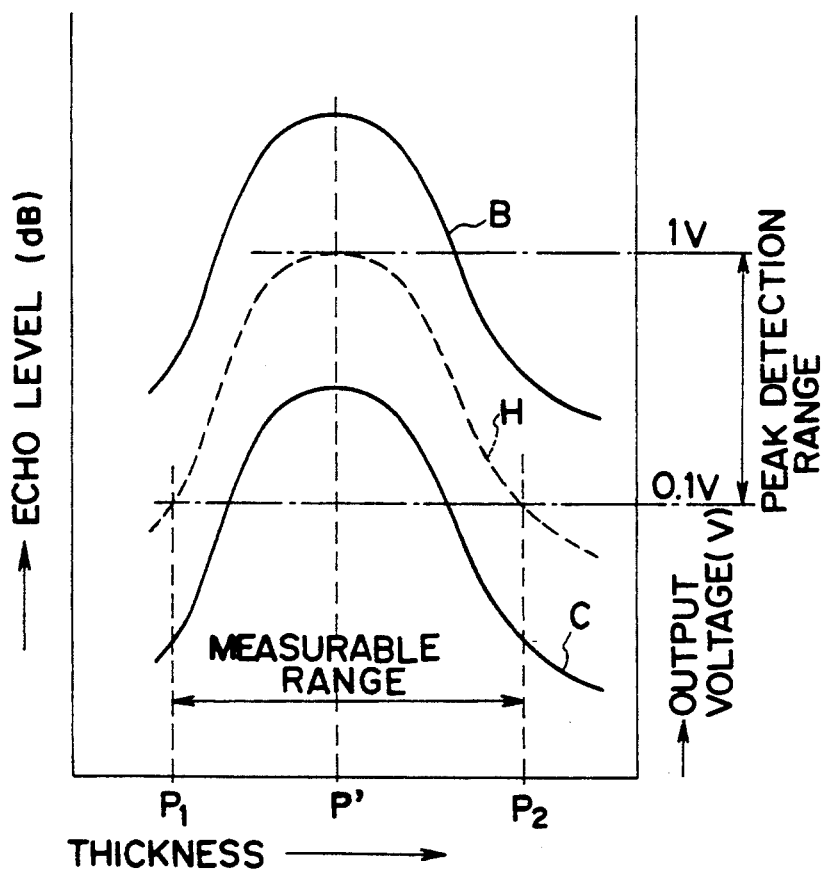
FIG. 3 is a graph showing variable ranges of amplitude level.

FIG. 3 is a graph wherein the variable range of amplitude level is illustrated. The abscissa denotes the thickness of the metals and the ordinates denote the echo level and the output voltage. The curve B denotes the total echo B, the curve C, the clad echo C, and the curve H, the amplified signal pattern of the curves B and C. At the thickness P', the curves B, C, and H have their maximum values.

As shown in FIG. 3, there is a difference between the signal level of the total echo B and that of the clad echo C. The signal pattern of the echo B and the signal pattern of the echo C are changed to the signal pattern H by the receiving amplifier 5 with the alternation of the amplitude.

The level of the signal pattern H is in the range of 0.1-1 volt which is a signal level easy to process in electronic circuits. The amplified outputs from the receiving amplifier 5 are transmitted to the gate selector 13 and the zero-crossing detector 14.

The gate controller 12 receives the time sharing signal from the time sharing controller 10 and transmits a control signal whereby the B gate generator generates the B gate signal at the timing when the receiving crystal 3b receives the total echo B, and a control signal whereby the C gate generator 8 generates the C gate signal at the timing when the receiving crystal 3b receives the clad echo C.

The B gate signal and the C gate signal are inputted to the gate selector 13. The gate selector 13 transmits the part of the amplified signal from the receiving amplifier 5, corresponding to the total echo B, to the peak detection circuit 16 when the gate selector 13 receives the B gate signal. The gate selector 13 transmits the part of the amplified signal from the receiving amplifier 5, corresponding to the clad echo C, to the peak detection circuit 16 when the gate selector 13 receives the C gate signal.

The peak detecting circuit 16 detects the peak of the amplified output which is inputted from the receiving amplifier 5 through the gate selector 13 and transmits the detected signal to the zero-crossing detecting circuit 14. The zero-crossing detecting circuit 14 receives the detected signal from the peak detecting circuit 16, detects the zero-crossing points of parts of the amplified signals corresponding to the echo B and the echo C from the receiving amplifier 5, and transmits the detected signal to the counter 9.

The counter 9 counts the clock signals generated by the clock generator 6. The counting starts when the counter 9 receives the zero signal generated by the zero adjustment unit 17 and ends when the counter 9 receives the detected signal from the zero-crossing detecting circuit 14. The zero point signal is generated by the zero adjustment unit 17 when the ultrasonic beam generated by the transmitter crystal 3a is radiated at the clad surface towards the inside of the clad metal 2. The counted value from the counter 9 is transmitted to the memory 18 and to the clad thickness calculator 19.

The clad thickness calculator 19 calculates the difference between the first calculated value which corresponds to the zero-crossing point of the amplified signal of the total echo B, and the second calculated value which corresponds to the zero-crossing point of the amplified signal of the clad echo C, and transmits the calculated difference value to the sonic velocity calculator 20.

The sonic velocity calculator 20 calculates the thickness of the clad metal 2 by multiplying the difference between the first and second calculated values, by the sonic velocity of the clad metal 2, and transmits the calculated result to the display 21.

The technique of the apparatus of the present invention is explained as follows. The measuring of the clad metal thickness is carried out by a twice repeated action, that is, the time of the total echo from zero point to zero-crossing point is counted at the first action, Ta period shown in FIG. 4 and FIG. 5, the time of the clad echo is counted at the second action, Tb period shown in FIG. 4 and FIG. 5, and the clad thickness is calculated and output thereafter from the difference between the time of the total echo stored in the memory. It is necessary to switch the amplitude of the receiving amplifier 5 at the time to receive the clad echo at the second period from that of at the time to receive the total echo at the first period because the level of the clad echo is lower than that of total echo. The amplitude of the receiving amplifier 5 is controlled by a time sharing signal from a time sharing controller 10.

The timing clock generator 7 transmits a trigger pulse to transmitter 4, zero adjustment unit 17, and time sharing controller 10, synchronizing the measuring start pulse to the closest phase of the clock pulse when a clock signal is received from clock generator 6. From this operation, the accurate counting of the received echo is achieved at the final counting point of the echo without any error. However, the trigger pulse transmitted to the time sharing controller 10 is not to be necessarily synchronized.

The transmitter 4 receives the timing signal for transmission and transmits a transmission pulse signal to the transmitting crystal 3a of the double crystal angle probe 3, whereby the transmitting crystal 3a radiates the ultrasonic pulse beam "T" to the mother metal 1. The radiated ultrasonic beam propagates in the mother metal 1, reaches the boundary surface between the mother metal and the clad metal, wherein a part of the beam is reflected as the clad echo C and the other part of the beam passes through the boundary surface, reaches the inner, bottom surface of the clad metal, and is reflected by the inner, bottom surface of the clad metal as the total echo B. The echo B and echo C then fall incident to the receiver crystal 3b.

The receiver crystal 3b generates the electric signal, the amplitude of which corresponds to the level of the clad echo C and the total echo B, after the incidence of the echo B and the echo C at the receiver crystal 3b. These signals are amplified by the receiving amplifier 5 and are transmitted to the gate selector 13 and to the zero-crossing detecting circuit 14.

Actually, the output of the receiving amplifier 5 is a radio frequency wave. The outputs of the receiving amplifier 5 are shown in the simplified pattern of a detected wave in FIGS. 2, 4, and 5.

The time sharing controller 10 receives the timing signal for transmission from the timing clock generator 7 and generates the time sharing signal at the timing when the receiving crystal 3b receives the signal of the total echo B and the clad echo C, and the time sharing signal is transmitted to the amplitude controller 11 and to the gate controller 12. The amplitude controller alternates the amplitude of the output of amplifier 5 in correspondence with the timing wherein the receiving crystal 3b receives the signals of the total echo B and the clad echo C.

Figure 4:
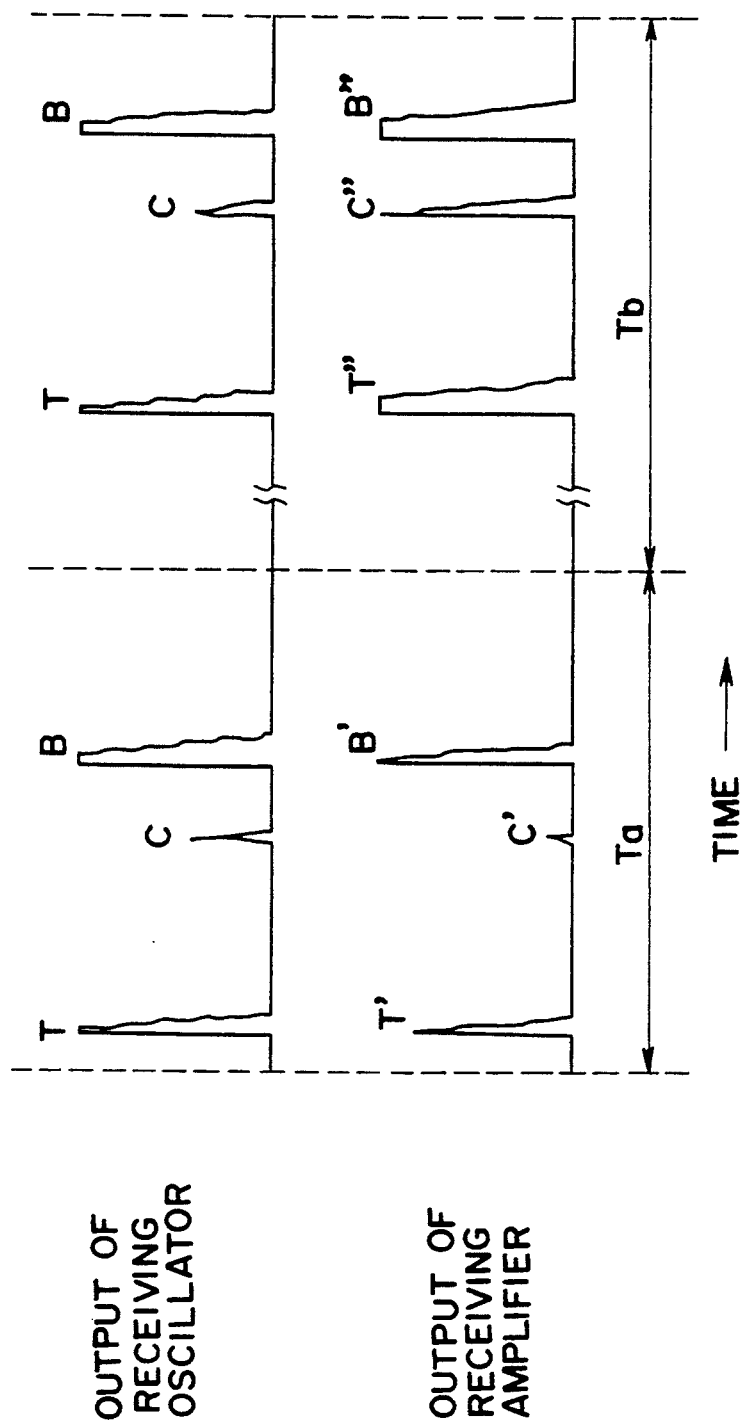
FIG. 4 shows the signal patterns before and after amplification.

FIG. 4 shows the signal pattern before and after the amplification. The upper part of FIG. 4 shows the signal pattern as the output of the receiver crystal 3b, or the output of the receiving oscillator, wherein the amplifier 5 does not alternate the amplitude by the amplitude controller 11. In this case the level of the signal of the echo B and the echo C in FIG. 4, corresponds to the signal level of the echo B and the echo C in FIG. 3 at the thickness of P'. The lower part of FIG. 4 shows the output of the receiving amplifier 5, or the amplified signal patterns of the echo B and the echo C wherein the receiving amplifier 5 alternates the amplitude by the signal from the amplitude controller 11.

As shown in FIG. 4, the amplitude of the receiving amplifier 5 is alternated to the value for the total echo B in the period Ta, wherein the level of the echo B is alternated to the level of H in FIG. 3. As the result of this amplification, the transmitting signal T, the total echo B, and the clad echo C are transformed to T', B', and C' respectively in the period of Ta. As shown in FIG. 4, the amplitude of the receiving amplifier 5 is alternated to the value for the clad echo C in the period Tb, wherein the level of the echo C is amplified to the level of H in FIG. 3. As the result of this amplification, the signals of the transmission T, the total thickness echo B, and the clad echo C are transformed to T'', B'', and C'' respectively in the period of Tb.

The time sharing signal is generated by the time sharing controller 10 and is transmitted to the B gate generator 15 and to the C gate generator 8 via the gate controller 12.

Figure 5:
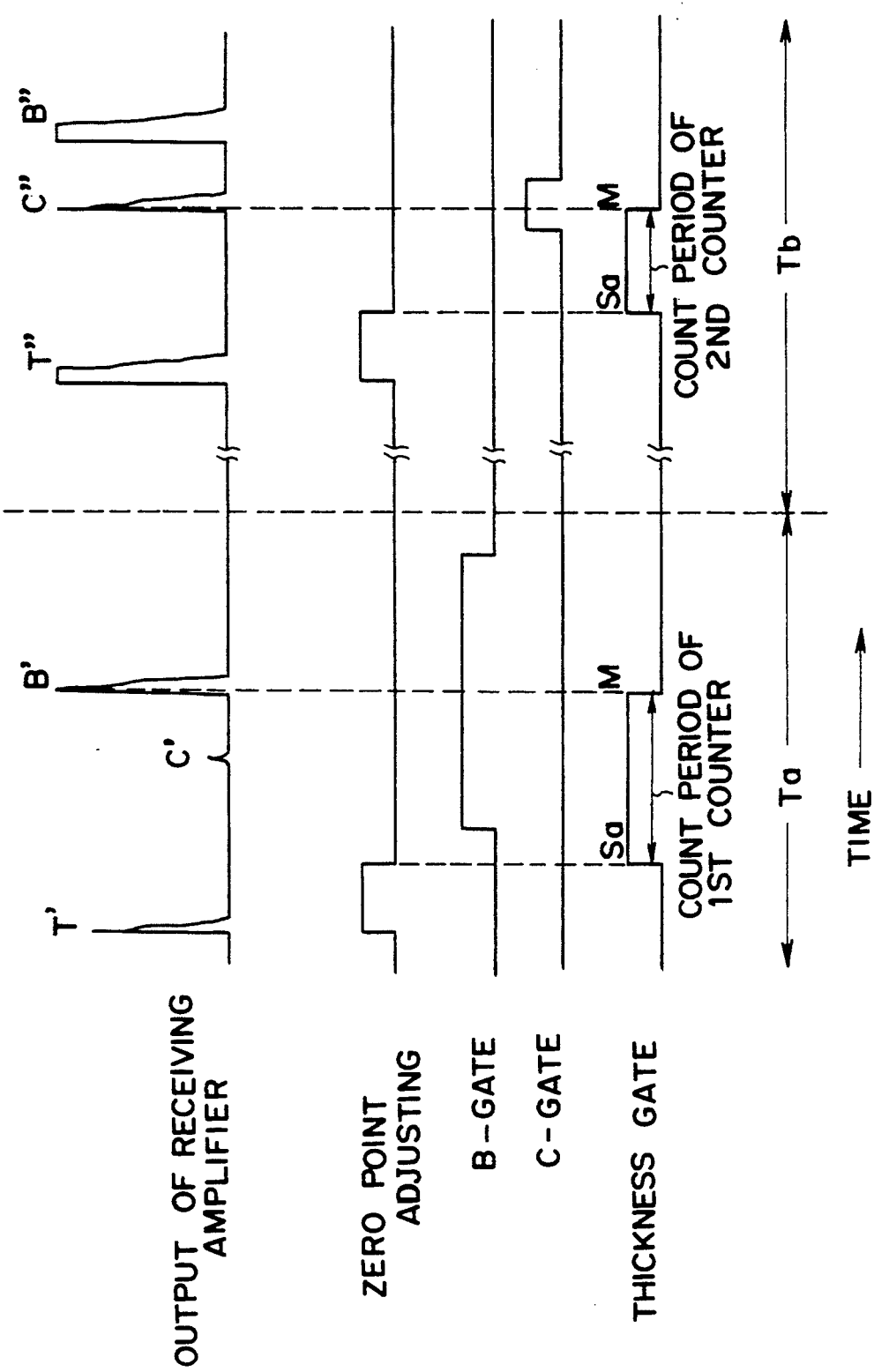
FIG. 5 shows a timing chart of the measurement of the total and clad thicknesses.

FIG. 5 is a graph which shows the timing chart of the measurement of the total and clad thicknesses. The abscissa denotes time. The first action is shown in period Ta, and the second action is shown in period Tb. The top curve shows the output of the receiving amplifier 5, or the amplified signal. The second curve shows the level of the zero point adjusting. The third curve shows the level of the output of the B gate. The fourth curve shows the level of the output of the C gate. The fifth curve shows the level of the output of the thickness gate.

As illustrated in FIG. 5, in the period Ta, the B gate generator 15 transmits the B gate signal to the gate selector 13 during the high level time of the B gate, wherein the total echo B' and the clad echo C' are included. The total echo B' and the clad echo C' are transmitted to the peak detecting circuit 16 via the gate selector 13. The B gate generator becomes high level in the thickness range from $P_1$, and $P_2$, in FIG. 3.

The peak detecting circuit 16 detects the peaks of the electrical signal of the total echo B' and the clad echo C' inputted through the gate selector 16. The action is similar in the period Tb.

The peak detecting circuit 16 detects the peaks of the electrical signal in the B gate period generated by the B gate generator 15 for the purpose of detecting the total echo at the first action, and that in the C gate period generated by the C gate generator 8 for the purpose of detecting the clad echo at the second action.

As the total echo level is comparatively higher than those of reflecting echo by the internal structure of the metal at the first action, the amplitude of the receiving amplifier 5 is only to be set so that the output should be in an appropriate range. On the other hand, the level of reflected echoes by the internal structure of the metal are so high compared with that of the clad echo in the second action that the clad echo cannot be distinguished among the echoes by conventional methods such as by an electric volts converter. However, by the present peak detecting circuit, the clad echo can be detected as the highest level of the wave of which output is shown as point Pk in FIG. 6.

Figure 6:
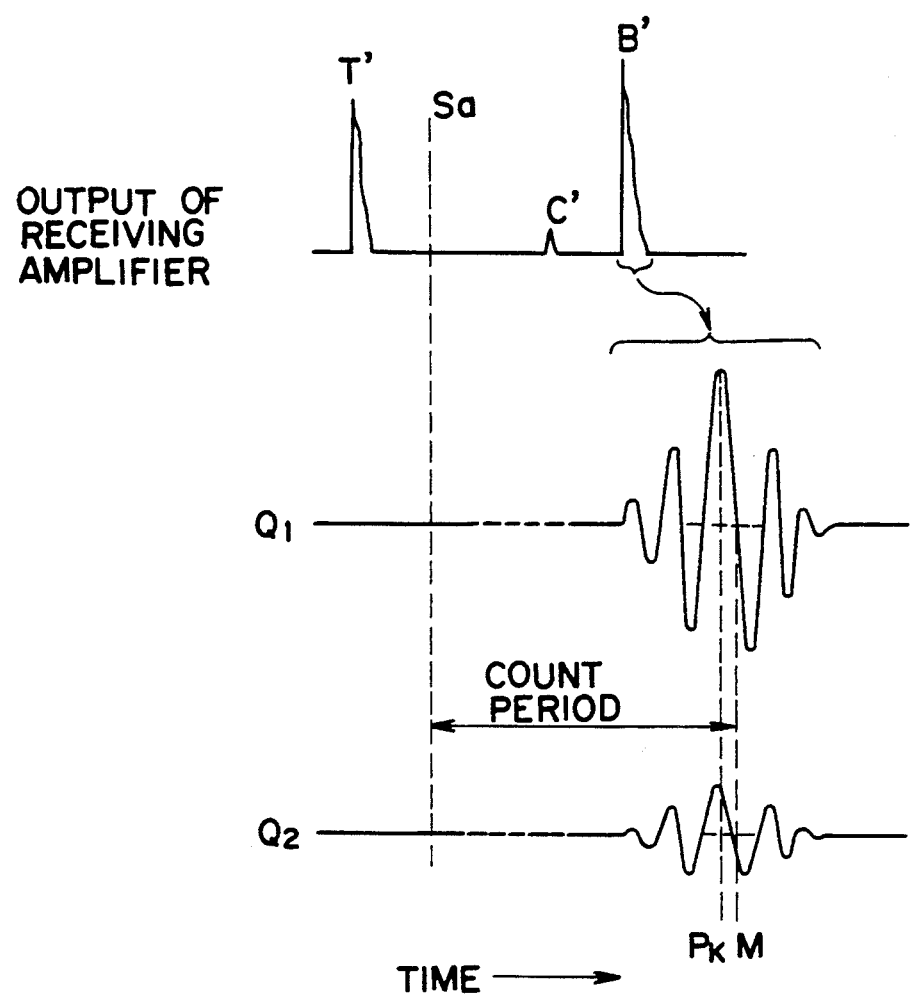
FIG. 6 shows a graph wherein the zero crossing point is illustrated.

FIG. 6 is a graph showing the zero-crossing point. The abscissa denotes time. The top curve shows the output of the receiving amplifier 5. The middle curve and the bottom curves show the radio frequency wave patterns of the total echo B.

As shown in FIG. 6, the radio frequency wave pattern of the detected wave of the receiving amplifier 5 are denoted as $Q_1$, and $Q_2$, as for the total echo B. The wave patterns $Q_1$ and $Q_2$ are enlarged as for the time direction. The wave pattern $Q_1$ is in the state of high level of which peak corresponds with the value of the echo level of the curve H of FIG. 3 at the thickness value of P' which is 1 volt as for the output voltage. The wave pattern $Q_2$, is in the state of low level of which the peak corresponds with the value of the echo level of the curve H of FIG. 3 at the thickness values of $P_1$, and $P_2$, which is 0.1 volt as for the output voltage. The curve H is the amplified echo B' which is the amplified signal of the total echo B, and also is the amplified echo C'' which is the amplified signal of the clad thickness echo C.

FIG. 6 also shows the radio frequency wave pattern of the B' echo in the period of Ta the wave pattern of which is analogous to the C'' echo in the period of Tb. The peak detecting circuit 16 detects $P_k$, as the peak time, and transmits the value to the zero-crossing detecting circuit 14 which detects the zero crossing time M. Since the voltage changing rate (dV/dt) is the lowest and the jitter is increased at the peak point, the zero-crossing detection circuit is put in an actuating state at the peak position and the output signal of the receiving amplifier 5 is transmitted to the zero-crossing detection circuit, thereby detecting the zero cross point (M) where the voltage changing rate (dV/Dt) becomes the greatest. As shown in FIG. 6, the time M for both wave patterns $Q_1$ and $Q_2$, is the same, irrespective of the difference between their levels, which leads to the accurate measurement of time.

The zero-crossing detection circuit 14, upon detecting the zero-crossing point, outputs the zero-crossing signal to the counter 9. The counter 9 has been counting the clock signal since it receives the zero point signal from the zero-adjustment unit 17 and until the zero-crossing signal is inputted to the counter 9. The time Sa when the counter 9 receives the zero point signal corresponds with the time when the ultrasonic beam by the transmitter crystal 3a is radiated into the surface of the mother metal 1.

The first counted value corresponds with the time from the time Sa, to the time when the zero-crossing signal is inputted to the counter 9. The first counted value is temporarily stored in the memory 18.

The C gate signal which becomes high level during the time including the clad echo C'' in the period of Tb, is generated at the C gate generator 8 in response to the time sharing signal from the time sharing controller 10. When the C gate signal is transmitted to the gate selector 13, the clad echo C'' is transmitted to the peak detecting circuit 16 via the gate selector 13.

The peak detecting circuit 16 detects the peak of the electric signal of the clad echo C'' and transmits the signal to the zero-crossing detecting circuit 14. The zero-crossing detecting circuit, upon receiving the peak signal, starts detecting the zero-crossing point of the output of the receiving amplifier 5 and the detected signal of the zero-crossing point is transmitted to the counter 9.

The counter 9 has been counting the clock signal since it received the zero point signal from the zero-adjustment unit 17 until the zero-crossing signal is inputted to the counter 9, whereby the second counted value is obtained.

When the first and the second counted values are obtained, these values are transmitted to the clad thickness calculator 19. The clad thickness calculator 19 calculates the difference between the first and the second counted values, and transmits the calculated value to the sonic velocity calculator 20. The sonic velocity calculator 20 calculates the thickness of the clad metal 2 by multiplying the difference by the sonic velocity of the clad metal and the calculated thickness is transmitted to the display 21 wherein the clad thickness is displayed.

As explained with reference to the above-directed embodiment, the output of the double crystal angle probe 3 is amplified to the amplitude corresponding with the total echo B and the clad echo C in response to the time sharing signal. The parts of the amplified signal which corresponds to the B echo and the C echo are selected out by the gate selector 13. The peak values and the zero-crossing points of the selected output signals are detected. The times from the zero-crossing points of the total echo and the clad echo, or the times required to receive these echoes are calculated and the clad thickness is obtained. Hence the non-destructive measurement of the total thickness and the clad metal thickness can be carried out from the outer surface of the clad material with respect to the total surface thereof with high efficiency, at low cost, and with high reliability.

As for the product of the clad metal, a clad tube is a good target of the present invention since the measurement is difficult from the inside of the tube.

As the material of the mother metal, low carbon steel or low alloy steel are widely used. As the material of the clad metal, stainless steel, nickel base alloy, and titanium base alloy are widely used.

As for the material of the crystal, the following is the most favorable for the measurement of clad materials:

(1) zirconium titanate series porcelain for the transmitting crystal and the receiver crystal;
(2) piezoelectric porcelain for the transmitting crystal and the receiver crystal;
(3) zirconium titanate series porcelain for the transmitting crystal and piezoelectric porcelain for the receiver crystal.

As for the dimensions of the probe, the most favorable is where the height is 5 mm and the width is 10 mm, or where the height is 10 mm and the width is 10 mm.

The angle of refraction preferably ranges from 35 degrees to 70 degrees. In the case where the thickness of the clad metal is above 10 mm, the angle of refraction preferably ranges from 35 degrees to 50 degrees. In the case where the thickness of the clad metal is below 10 mm, the angle of refraction preferably ranges from 50 degrees to 75 degrees.

The frequency range preferably utilized in this invention is from 2 to 10 MHz.

The coupling methods for acoustically coupling the probe and the measured body are the contact method and the water column coupling method.

In the case of a measurement of a clad tube, the following are preferably the conditions of the scanning:

(1) The double crystal angle probe is stationary and the tube is spirally moved;
(2) The tube moves straight and the double crystal angle probe is rotated.

What is claimed is:

1. An apparatus for measuring the thickness of a clad material, said clad material comprising a clad metal and a mother metal, said clad metal having an outer surface and an inner surface, said mother metal having an outer and an inner surface, said clad metal being clad to said mother metal such that the outer surface of said clad metal and the inner surface of said mother metal form a boundary surface, said apparatus comprising:

a double crystal angle probe contacting the outer surface of said mother metal, said double crystal angle probe comprising:
  a transmitter crystal means for radiating a plurality of ultrasonic beams into said clad material; and
  a receiver crystal means for receiving a first echo of an ultrasonic beam from the boundary surface of said mother metal and clad metal, for receiving a second echo of the ultrasonic beam from the inner surface of said clad metal, and for producing first and second echo signals, respectively;
amplifying means for amplifying said first echo signal with a first amplitude value, and for amplifying said second echo signal with a second amplitude value, said amplifying means being responsive to first and second time sharing signals for alternately amplifying said first and second echo signals with said first amplitude value and said second amplitude value;
zero point determining means for determining a zero point of time when the transmitter crystal means radiates an ultrasonic beam into said clad material;
time sharing means for generating said first time sharing signal and said second time sharing signal at predetermined timings;
detecting means for detecting a time when said amplified first echo signal reaches a first zero-crossing point after a peak of said amplified first echo signal, and for detecting a time when said amplified second echo signal reaches a first zero-crossing point after a peak of said amplified second echo signal;
period calculating means for calculating a first time period from the zero point of time determined by said zero point determining means to the first zero-crossing point of said amplified first echo signal, and for calculating a second time period from the zero point of time to the first zero-crossing point of said amplified second echo signal; and
thickness calculating means for calculating the thickness of said clad metal and the total thickness of said clad material as a function of said calculated first time period and said calculated second time period.

2. The apparatus of claim 1, wherein said clad material comprises a mother metal tube and a clad metal tube clad inside said mother metal tube.

3. The apparatus of claim 2, wherein said clad metal is a stainless steel and said mother material is a low carbon steel.

4. The apparatus of claim 2, wherein said clad metal is a stainless steel and said mother metal is a low alloy steel.

5. The apparatus of claim 2, wherein said clad metal is a nickel base alloy and said mother metal is a low carbon steel.

6. The apparatus of claim 2, wherein said clad metal is a nickel base alloy and said mother metal is a low alloy steel.

7. The apparatus of claim 2, wherein said clad metal is a titanium base alloy and said mother metal is a low carbon steel.

8. The apparatus of claim 2, wherein said clad metal is a titanium base alloy and said mother metal is a low alloy steel.

9. The apparatus of claim 1, wherein said transmitting crystal means and said receiver crystal means comprise zirconium titanate series porcelain.

10. The apparatus of claim 1, wherein said transmitting crystal means and said receiver crystal means comprise piezoelectric porcelain.

11. The apparatus of claim 1, wherein said transmitting crystal means comprises zirconium titanate series porcelain, and said receiver crystal means comprises piezoelectric porcelain.

12. The apparatus of claim 1, wherein said transmitting crystal means and said receiver crystal means are about 5 mm in height and about 10 mm in width.

13. The apparatus of claim 1, wherein said transmitting crystal means and said receiver crystal means are about 10 mm in height and about 10 mm in width.

14. The apparatus of claim 1, wherein the range of the frequency utilized in said transmitting crystal means and said receiver crystal means is from 2 to 10 MHz.

15. The apparatus of claim 1, wherein said double crystal angle probe is stationary, and said clad material is spirally moved relative to said double crystal angle probe in a scanning direction.

16. The apparatus of claim 1, wherein said clad material is moved in a substantially straight direction, and said double crystal angle probe is rotated to perform scanning of said clad material.

17. The apparatus of claim 1, further comprising gating means for gating said amplified first echo signal and said amplified second echo signal to said detecting means.

* * * * *